United States Patent [19]

Henry

[11] 4,330,509

[45] May 18, 1982

[54] SEPARATION OF ZIRCONIUM AND URANIUM

[75] Inventor: Helen G. Henry, Reno, Nev.

[73] Assignee: The United States of America as represented by the Secretary of the Interior, Washington, D.C.

[21] Appl. No.: 266,225

[22] Filed: May 22, 1981

[51] Int. Cl.$^3$ .............................................. C01G 25/00
[52] U.S. Cl. ....................................... 423/85; 423/11; 423/608; 260/429.3
[58] Field of Search ........................... 423/11, 85, 608; 260/429.3; 562/585

[56] References Cited

U.S. PATENT DOCUMENTS

| 1,624,162 | 4/1927 | de Boer | 423/608 |
| 2,967,088 | 1/1961 | Peters | 260/429.3 |
| 2,982,600 | 5/1961 | Vogler | 260/429.3 |

OTHER PUBLICATIONS

"Chem. Abst.", vol. 44, 1950, p. 10600e.

Primary Examiner—G. O. Peters
Attorney, Agent, or Firm—William S. Brown; Donald A. Gardiner

[57] ABSTRACT

Zirconium is selectively precipitated from aqueous solutions containing zirconium and uranium by treatment with a precipitant consisting of tartaric acid or a tartrate.

4 Claims, No Drawings

SEPARATION OF ZIRCONIUM AND URANIUM

This invention relates to separation and recovery of zirconium from aqueous solutions containing zirconium and uranium. Such solutions are typically those formed by the processes disclosed in U.S. Pat. Nos. 3,658,466 and 4,231,994. Those processes involve initial sulfuric acid leaching of zircon sands to extract zirconium, along with hafnium and uranium which are commonly present in the sands. Recovery of zirconium, with substantial separation from hafnium, is then accomplished by solvent extraction with an organic amine, followed by stripping with sodium chloride solution to remove the zirconium from the organic phase.

Separation of zirconium from uranium is, however, difficult since the uranium tends to accompany the zirconium in the solvent extraction and stripping steps. It is therefor desirable, and an object of the invention, to provide a simple and economical way of removing a major portion of the zirconium from the zirconium and uranium-containing strip solutions, with minimal removal of uranium. This is particularly desirable for production of nucleargrade zirconium, in which the uranium content must be reduced to 3 ppm or less in the final product.

It has now been found, according to the present invention, that such a removal of zirconium may be accomplished by means of a process involving precipitation of zirconium from such zirconium and uranium-containing feed solutions by means of tartaric acid or a tartrate. Tartaric acid or ammonium tartrate are the preferred precipitants, but other tartrates such as sodium tartrate may be used.

Precipitation of zirconium from the feed solution is accomplished by addition of precipitant in an amount, usually approximately stoichiometric, sufficient for maximum precipitation of zirconium, with minimal precipitation of uranium. When the feed solution consists of a strip solution of the type discussed above, the amount of precipitant will usually range from about 0.05 to 0.3 mole. The precipitant is added with agitation, such as stirring, of the solution, and ambient conditions of temperature and pressure are usually satisfactory. The pH of the feed is not critical, but will usually range from about 0.2 to 1.0. Addition of about 20 to 30 volume percent of methanol with, or following addition of, the precipitant is also usually desirable for the purpose of speeding settling and facilitating filtering of the flocculant precipitate.

Subsequent treatment of the zirconium tartrate precipitate will ordinarily consist of conversion to $ZrO_2$ by conventional means such as roasting, with the $ZrO_2$ ultimately being used as a feed material to make zirconium sponge.

The invention will be more specifically illustrated by the following examples.

EXAMPLE 1

A feed solution from a solvent extraction process for recovery of zirconium from zircon sands was treated according to the process of the invention. The feed consisted of a strip liquor obtained from use of a 1.5 molar NaCl strip solution to strip zirconium from a zirconium-loaded amine extractant. The strip liquor contained 23 g/l zirconium, 12 ppm uranium relative to zirconium, 3.8 g/l chloride, 120 g/l sulfate, and was 0.44 normal with respect to hydrogen ion.

Ammonium tartrate in the amount of 10.6 grams was dissolved in 200 ml of the feed, and a 25 ml portion of methanol was added with stirring. A white precipitate was formed. After 20 minutes of standing, another 25 ml portion of methanol was added. After 45 minutes of additional stirring, the precipitate was permitted to settle for one and one-half hours, and the resulting amorphous precipitate was filtered, washed with two 25 ml portions of methanol and dried at 125° C.

X-ray diffraction studies identified the major component of the precipitate as a zirconium tartrate compound containing approximately 27.5 to 27.7 percent zirconium. Eighty percent of the zirconium in the feed solution was thus recovered as precipitate, and the dried precipitate contained 2.78 ppm uranium relative to zirconium.

EXAMPLE 2

A feed solution from a solvent extraction process for recovery of zirconium from zircon sands was treated according to the process of the invention. The feed consisted of a strip liquor obtained from use of a 1.5 molar NaCl strip solution to strip zirconium from a zirconium-loaded amine extractant. The strip liquor contained 13 g/l zirconium, 10 ppm uranium relative to zirconium, 25 g/l chloride, 70 g/l sulfate, and was 0.20 normal with respect to hydrogen ion.

Tartaric acid in the amount of 2.58 grams was dissolved in 200 ml of the feed, and a 25 ml portion of methanol was added with stirring. A white precipitate was formed. After 20 minutes of standing, another 25 ml portion of methanol was added. The solution is stirred intermittently. After aging overnight, the resulting amorphous precipitate was filtered, washed with two 25 ml portions of methanol and dried at 125° C.

X-ray diffraction studies identified the major component of the precipitate as a zirconium tartrate compound containing approximately 27.5 to 27.7 percent zirconium. Sixty-three percent of the zirconium in the feed solution was thus recovered as precipitate, and the dried precipitate contained <1.9 ppm uranium relative to zirconium.

I claim:

1. A method for separation and recovery of zirconium from a feed consisting of an aqueous solution of zirconium and uranium having a pH of about 0.2 to 1.0 comprising treatment of the solution with a precipitant consisting of tartaric acid or a tartrate, the amount of said precipitant being sufficient to selectively precipitate zirconium as a tartrate with minimal precipitation of uranium.

2. The method of claim 1 in which the precipitant is tartaric acid.

3. The method of claim 1 in which the precipitant is ammonium tartrate.

4. The method of claim 1 in which the feed solution consists of a strip liquor from a solvent extraction process for recovery of zirconium from zircon sands.

* * * * *